United States Patent [19]

Neumann et al.

[11] Patent Number: 5,710,625
[45] Date of Patent: Jan. 20, 1998

[54] SPECTRAL OIL IMMERSION CELL

[75] Inventors: Margarete Neumann, Penetanguishene; Robert Pursel, Victoria Harbor, both of Canada

[73] Assignee: Hughes Electronics, Los Angeles, Calif.

[21] Appl. No.: 641,245
[22] Filed: Apr. 30, 1996
[51] Int. Cl.[6] ................................................. G01N 21/01
[52] U.S. Cl. ............................ 356/244; 356/440; 356/73
[58] Field of Search ................................. 356/244, 246, 356/30, 31, 440, 73; 250/573, 576

[56] References Cited

U.S. PATENT DOCUMENTS

| | | | |
|---|---|---|---|
| 2,352,072 | 6/1944 | Bond | 356/31 |
| 2,387,825 | 10/1945 | Bond | 356/31 |
| 2,497,070 | 2/1950 | Coleman | 356/31 |
| 3,523,738 | 8/1970 | Chisholm | 356/246 |
| 3,529,896 | 9/1970 | Padawer | 356/246 |
| 5,104,218 | 4/1992 | Garner | 356/244 |
| 5,422,718 | 6/1995 | Anderson | 356/244 |
| 5,463,466 | 10/1995 | Svendsen | 356/440 |
| 5,594,545 | 1/1997 | Saito et al. | 356/440 |

*Primary Examiner*—Hoa Q. Pham
*Attorney, Agent, or Firm*—Gordon R. Lindeen, III; Michael W. Sales; Wanda K. Denson-Low

[57] ABSTRACT

A device for holding and positioning a sample (22) during spectral analysis, having an optical cell (41) comprised of a base member (42), a glass cell (44), and being filled with oil (46) having substantially the same index of refraction as the glass cell (44). The device further includes a rotary stage device (48) attached to the optical cell (41) and a sample holder (50) attached to the rotary stage device (48) such that a sample (22) may be rotated over a range of angles relative to a projected beam (32) to provide a spectral analysis of the sample (22) over the range of angles.

20 Claims, 2 Drawing Sheets

SPECTRAL OIL IMMERSION CELL

BACKGROUND OF THE INVENTION

1. Technical Field

The present invention relates to optical analysis testing equipment and, more particularly, to a spectral oil immersion cell used in measuring the spectral performance of a coating over a range of angles.

2. Discussion Of Related Art

The performance requirements of coatings designed for optical media other than air is often specified over a range of angles. The measurement over a given range of angles previously required multiple sets of prism pairs manufactured for each desired measurement angle. A sample to be tested is attached between the hypotenuse of the prism pairs and the prisms are then fastened to one another along their hypotenuses. This assembly is placed in a spectrophotometer sample compartment, a beam projected through the assembly, and the transmitted and reflected components of the beam are measured by detectors to determine the optical properties of the sample. Prior to measuring the components of the beam with the sample in place, the prism pair must be assembled without the sample in place to set the spectrophotometer reference spectrum and adjust the detectors to read a 100 percent transmission level.

After determining the transmission spectrum of the sample at the first angle, the prism pair is separated and the sample is attached to a new prism pair having a different angle. Again, prior to testing the sample, the prism pair is assembled without the sample in place and the spectrophotometer reference spectrum and a 100 percent transmission level are set. Obviously, the process of assembling the prism pair, setting the spectrophotometer reference spectrum and a 100 percent transmission level, disassembling the prism pair, assembling the prism pair with a sample attached to the hypotenuse therebetween, and testing the coating sample at the particular angle of the prism pair can become a time consuming and labor intensive task when the performance of the sample over a plurality of angles is required.

SUMMARY OF THE INVENTION

The spectral oil immersion cell of the present invention employs a glass cell, substantially filled with oil having an index of refraction substantially the same as that of the glass cell which acts in place of a prism pair used to hold coating samples during spectral analysis in a spectrophotometer. Further, by attaching the coating sample to a rotary stage device, the sample, submerged in the oil within the glass cell, can be accurately rotated to multiple angles of incidence without the necessity of setting the spectrophotometer reference spectrum and the 100 percent transmission level between each test angle.

In the preferred embodiment, the spectral oil immersion cell is comprised of an optical cell having an inner chamber, a rotary stage device connected to the optical cell, and a sample holder which is attached to the rotary stage device and extends into the interior chamber. The optical cell is filled with oil having substantially the same index of refraction as the glass of the optical cell and the sample, attached to the sample holder, is submerged in the oil. By utilizing the present invention for holding a coating sample whose spectral performance is to be measured over a range of angles, the time consuming steps of the current method may be avoided since the spectrophotometer reference spectrum and the 100 percent transmission level is set only once before insertion of the sample. Once the sample is in place within the optical cell, measurements can be performed at any desired angle through adjustment of the rotary stage which is less labor intensive and more accurate, since the optical alignment is not disturbed, than using a prism pair for each angle.

BRIEF DESCRIPTION OF THE DRAWINGS

The various advantages of the present invention will become apparent to one skilled in the art upon reading the following specification and by reference to the drawings in which.

DESCRIPTION OF THE PREFERRED EMBODIMENTS

Figure 1:
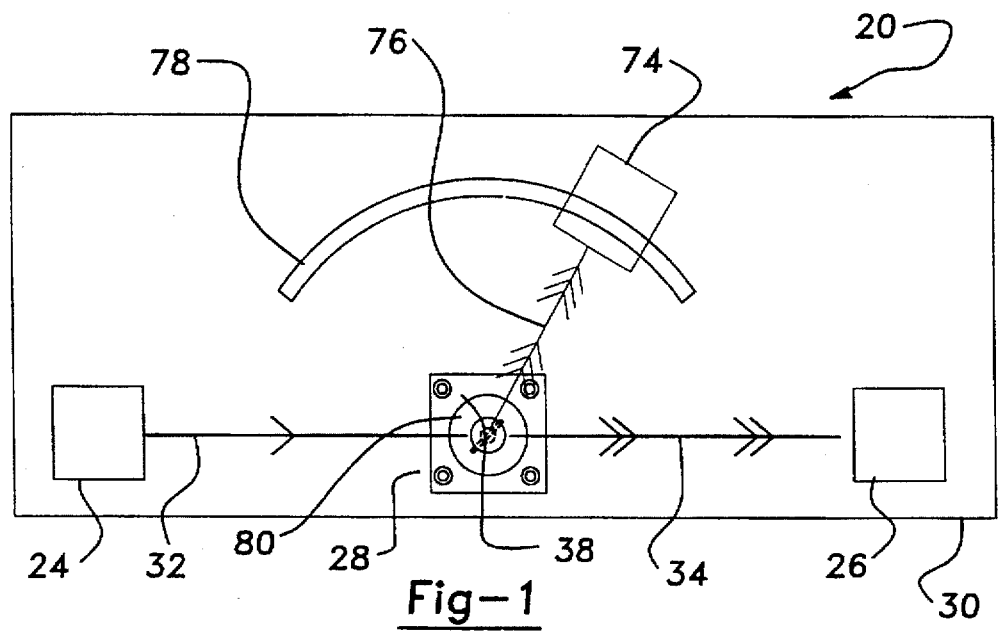
FIG. 1 is a block diagram of an apparatus incorporating the teachings of the present invention.

Turning to FIG. 1, there is shown a testing apparatus 20 for determining the optical performance of a coating sample 22. Apparatus 20 is comprised of a fixed beam generator 24, a first detector 26, and a sample holding device 28, all of which are mounted to a platform 30.

Beam generator 24 creates an optical beam 32 of known properties and is aligned with first detector 26 which measures the spectral properties of beam 32. Coating sample 22 is held within sample holding device 28 and is aligned such that beam 32 impinges upon sample 22. With sample 22 in such a position, first detector 26 measures a component of beam 32 which is transmitted through sample 22, such a component being identified as transmitted component 34.

Figure 2:
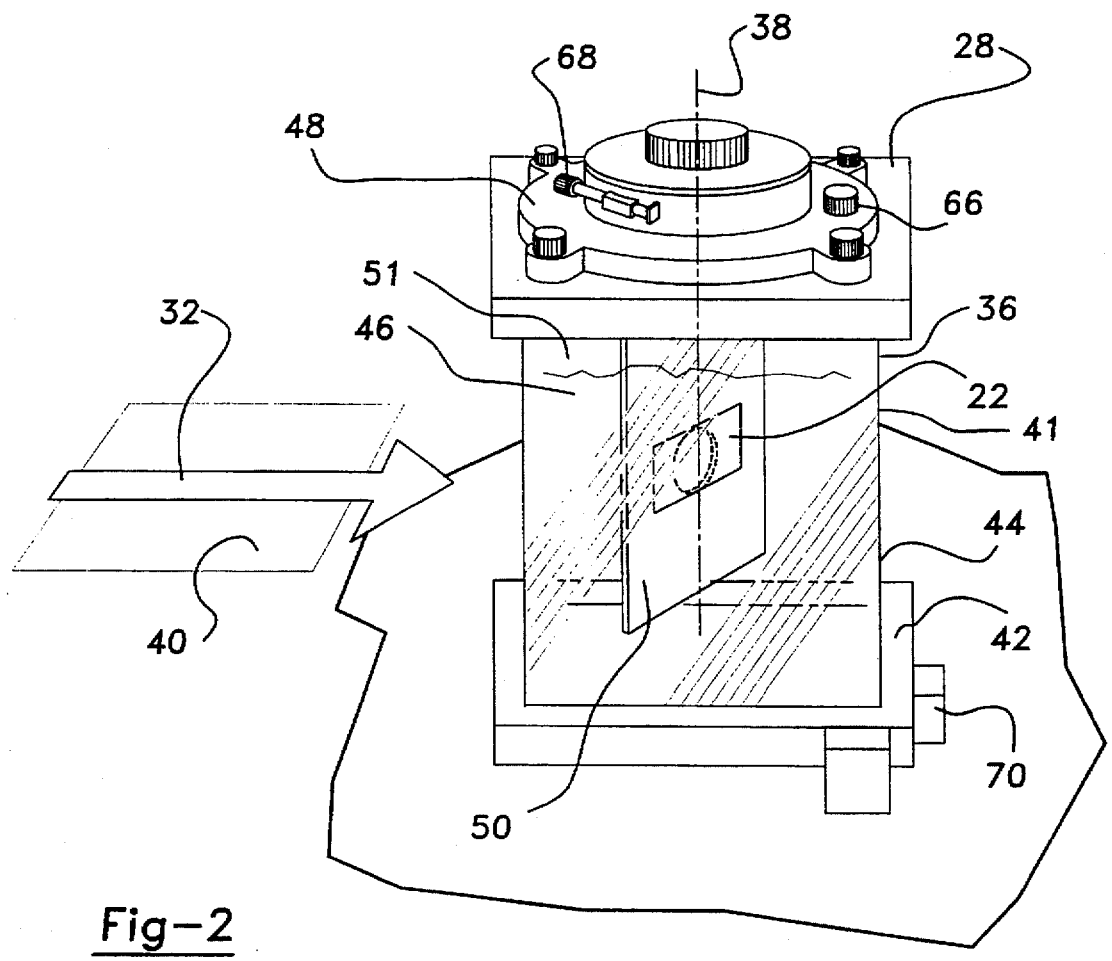
FIG. 2 is a perspective view of a preferred embodiment of the sample holding device of the present invention.

Referring to FIG. 2, sample holding device 28 of the present invention is comprised of a spectral oil immersion cell (SOIC) 36 which provides for rotation of sample 22 about an axis 38 which is perpendicular to a generally horizontal plane of incidence 40 created by beam 32. SOIC 36 includes an optical cell 41 having a base member 42, a glass cell 44 having a given index of refraction, and oil 46 having an index of refraction substantially matching that of glass cell 44; a rotary stage device 48 removably secured to the top of glass cell 44; and a sample holder 50 which is attached to rotary stage device 48 and provides for holding sample 22.

Glass cell 44 is typically constructed of polished plates of optical glass fastened to one another such that opposite sides of glass cell 44 are parallel to one another. While the preferred embodiment is depicted as a square, other quadrilaterals (such as a rectangle) or polygons having even numbered sides could also be utilized. Regardless of the particular shape, glass cell 44 is attached to base member 42 thereby creating an interior chamber 51 which is filled with oil 46 when SOIC 36 is in use. Since oil 46 and glass cell 44 have substantially the same index of refraction as one another, the combination functions in the same manner as a solid block of glass having that same index of refraction. Therefore, the matched sets of 90 degree prisms utilized in the prior art can be replaced with SOIC 36 which functions in the same manner.

The advantage of SOIC 36 over the prior art becomes readily apparent when sample 22 must be tested over a range of angles. As previously described, the prior art conventionally required multiple sets of paired prisms, with each set adapted for a particular angle of incidence. However, by rotating rotary stage device 48 about axis 38, sample 22 can be tested at a plurality of angles of incidence relative to beam 32 without remounting sample 22 and without resetting the spectral properties of beam 32 as in the aforementioned prior art.

Figure 3:
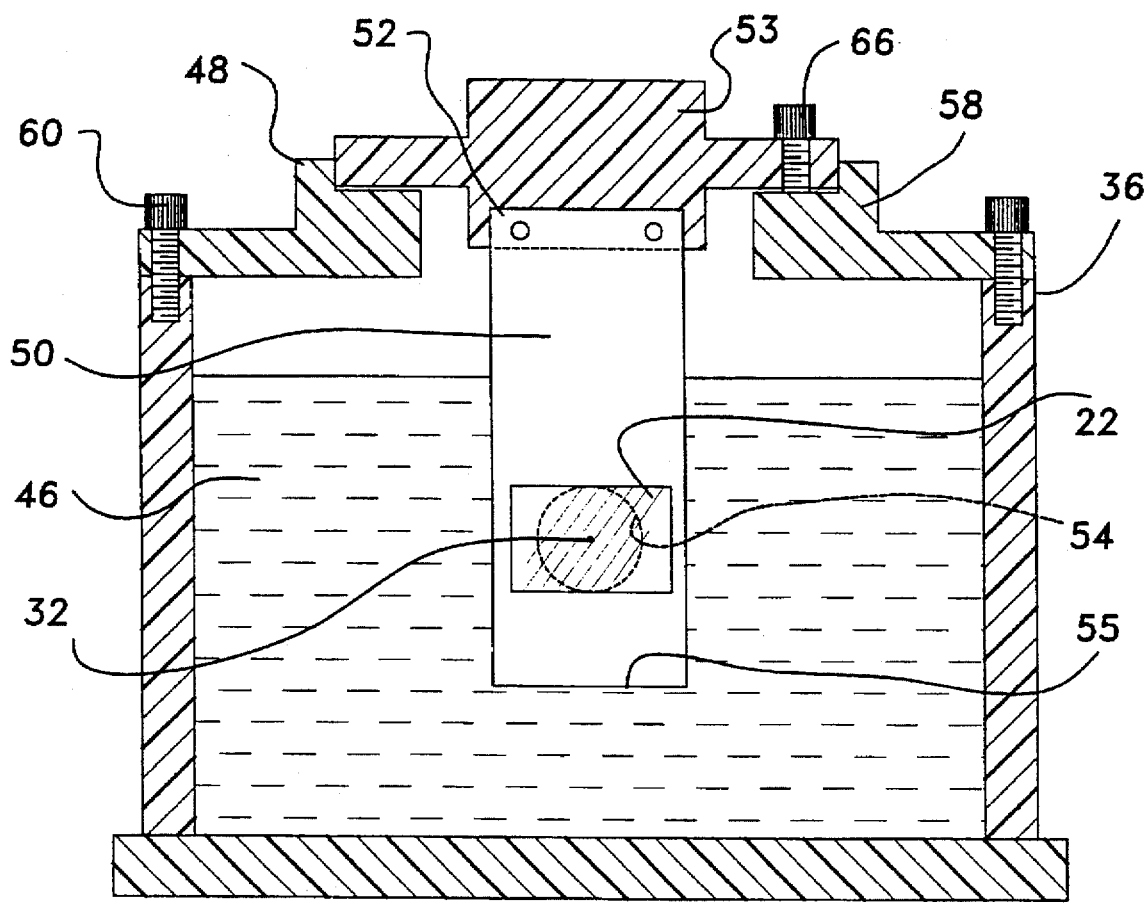
FIG. 3 is a sectional view of the sample holding device shown in FIG. 2.

FIG. 3 shows that sample holder 50 is preferably an elongated rectangular piece of material, such as black anodized aluminum or glass, which is attached along its top end 52 to rotatable portion 53 of rotary stage device 48. Holder 50 provides an aperture 54 near its lower end 55 and coating sample 22 is attached (e.g. by adhesives, clamping, or other method) to sample holder 50 such that sample 22 covers aperture 54. Aperture 54 is provided so that beam 32 passes through sample 22 only and a true spectral performance is determined, as opposed to introducing an additional layer of material positioned at an angle to beam 32 which would effect the transmitted component 34 measured by first detector 26. Aperture 54 is positioned such that sample 22 is submerged in oil 46 when SOIC 36 is assembled and in use.

Referring again to FIGS. 2 and 3, rotary stage device 48 includes a fixed portion 58 in addition to rotatable portion 53. Fixed portion 58 is secured to glass cell 44 by clamp screws 60 such that fixed portion 58 does not move relative to glass cell 44 when rotatable portion 53 is moved from a first angle of incidence position to a second angle of incidence position. In order to determine the angle of incidence between beam 32 and coating sample 22, rotary stage device 48 is engraved with angle indication marks (not shown) which are calibrated relative to beam 32. The rotary stage device 48 utilized in the preferred embodiment utilizes a coarse adjustment setting 66 which can be locked when the angle is near to the desired angle of incidence, and a fine micrometer adjustment screw 68 allowing for an angular accuracy of one-minute of arc. To provide repeated accuracy, base member 42 is aligned by locators 70 which are positioned relative to beam generator 24 and are attached to platform 30.

As shown in FIG. 1, an optional second detector 74 is used to measure a reflected component 76 of beam 32. Second detector 74 is movably positioned along an arc 78 centered about axis 38. The position of second detector 74 along arc 78 is determined by the angle of incidence between beam 32 and sample 22. The reflected component 76 of beam 32 is reflected from sample 22 at an angle equal to twice the angle between a normal line 80 which is perpendicular to the surface of sample 22 and beam 32. For example if the angle of incidence to sample 22 is 55 degrees relative to beam 32, then since the angle of incidence equals the angle of reflection, second detector 74 is positioned along arc 78 at 110 degrees from beam 32. Second detector 74 may be used alone or in conjunction with first detector 26 depending upon the characteristics of the spectral performance of sample 22 which are to be measured.

The foregoing discussion discloses and describes exemplary embodiments of the present invention. One skilled in the art will readily recognize from such discussion, and from the accompanying drawings and claims that various changes, modifications, and variations can be made therein without departing from the true spirit and fair scope of the invention as defined in the following claims.

What is claimed is:

1. A spectral oil immersion cell for holding and positioning a sample during spectral analysis in which a beam is projected at the sample, said spectral oil immersion cell comprising:

an optical cell including a glass cell having a given index of refraction and being substantially filled with an oil having substantially the same index of refraction as said glass cell so that said optical cell effectively functions as a solid block of glass;

a rotary stage device being connected to said optical cell; and a sample holder for holding said sample, said sample holder being attached to said rotary stage device and projecting into an interior chamber of said optical cell, said interior chamber being formed by said glass cell and a base member, wherein rotation of said sample allows for measurement of a spectral performance of said sample over a range of angles relative to said beam.

2. The spectral oil immersion cell of claim 1 wherein said glass cell is constructed such that opposite sides of said glass cell are parallel.

3. The spectral oil immersion cell of claim 2 wherein said sample holder is attached to said rotary stage device such that said sample is rotatable about an axis which is perpendicular to a plane of incidence created by said beam.

4. The spectral oil immersion cell of claim 3 wherein said rotary stage device includes a rotatable portion rotatable relative to said beam about an axis perpendicular to said plane of incidence, said rotatable portion being attachable to said optical cell and having said sample holder attached thereto.

5. The spectral oil immersion cell of claim 3 wherein said rotary stage device includes a fixed portion attached to said glass cell, and a rotatable portion being rotatable relative to said fixed portion and having said sample holder attached thereto.

6. The spectral oil immersion cell of claim 5 wherein said fixed portion and said rotatable portion have a course adjustment for approximately setting the angle between said fixed and rotatable portions, and a fine adjustment for accurately setting said angle to within one-minute of arc.

7. The spectral oil immersion cell of claim 1 wherein said sample holder is black anodized aluminum.

8. The spectral oil immersion cell of claim 1 wherein said sample holder is glass.

9. A method for supporting and testing the spectral properties of a sample, said method comprising:

providing an optical cell having walls with a given index of refraction, and creating an interior chamber therein;

filling said optical cell with an oil having substantially the same index of refraction as said walls;

attaching said sample to a sample holder;

placing said sample holder into said interior chamber such that said sample is submerged in said oil;

rotating said sample holder to a first position;

transmitting a first beam from a fixed beam generator at said optical cell such that said first beam passes through said walls and said oil, and impinges upon said sample;

detecting a first component of said first beam with a first detector;

rotating said sample holder to a second position;

transmitting a second beam from said fixed beam generator at said optical cell such that said second beam passes through said walls and said oil, and impinges upon said sample; and detecting a first component of said second beam with said first detector.

10. The method of claim 9 wherein said component of said first beam detected by said first detector is a transmitted component, and said component of said second beam detected by said first detector is a transmitted component.

11. The method of claim 9 wherein said component of said first beam detected by said first detector is a reflected component, and said component of said second beam detected by said first detector is a reflected component.

12. The method of claim 9 further comprising:

detecting a second component of said first beam with a second detector; and detecting a second component of said second beam with said second detector wherein said first component of said first beam and said second beam is a transmitted component, and said second component of said first beam and said second beam is a reflected component.

13. An apparatus for testing the optical performance of a sample over a range of angles, said apparatus comprising:

a fixed beam generator for creating a beam;

a first detector for detecting a transmitted component of said beam;

a sample holding device having a cell with a given index of refraction and being substantially filled with an oil having substantially the same index of refraction as said cell, said sample holding device providing for rotation of said sample about an axis perpendicular to a plane of incidence created by said beam wherein said beam, having known properties, is projected at said sample and impinges upon said sample, said transmitted component of said beam being detected by said first detector after said beam impinges upon said sample.

14. The apparatus of claim 13 further comprising: a second detector movably positioned relative to said beam generator, said second detector position being determined by an angle between said beam and a normal to the surface of said sample, wherein said second detector detects a reflected component of said beam after said beam impinges upon said sample.

15. The apparatus of claim 13 wherein said sample holding device further comprises:

a base member;

said cell being a glass cell being constructed such that opposite sides of said glass cell are parallel, said glass cell being attached to said base member and forming an interior chamber therein;

a rotary stage device being connected to said glass cell; and a sample holder for holding said sample, said sample holder being attached to said rotary stage device and extending into said interior chamber such that a sample attached to said sample holder is submerged in said oil.

16. The apparatus of claim 15 wherein said rotary stage device includes a rotatable portion rotatable relative to said beam about an axis perpendicular to said plane of incidence, said rotatable portion being attachable to said glass cell and having said sample holder attached thereto.

17. The apparatus of claim 15 wherein said rotary stage device includes a fixed portion attached to said glass cell, and a rotatable portion being rotatable relative to said fixed portion and having said sample holder attached thereto.

18. The apparatus of claim 17 wherein said fixed portion and said rotatable portion have a course adjustment for approximately setting the angle between said fixed and rotatable portions, and a fine adjustment for accurately setting said angle within one-minute of arc.

19. The apparatus of claim 15 wherein said sample holder is black anodized aluminum.

20. The apparatus of claim 15 wherein said sample holder is glass.

* * * * *